United States Patent
Kawakami et al.

(10) Patent No.: US 11,602,499 B2
(45) Date of Patent: Mar. 14, 2023

(54) COMPOSITION FOR KERATIN FIBERS

(71) Applicant: L'OREAL, Paris (FR)

(72) Inventors: Kazumitsu Kawakami, Kawasaki (JP); Akiomi Nakajima, Kawasaki (JP)

(73) Assignee: L'OREAL, Paris (FR)

( * ) Notice: Subject to any disclaimer, the term of this patent is extended or adjusted under 35 U.S.C. 154(b) by 167 days.

(21) Appl. No.: 16/617,243

(22) PCT Filed: May 11, 2018

(86) PCT No.: PCT/JP2018/019210
§ 371 (c)(1),
(2) Date: Nov. 26, 2019

(87) PCT Pub. No.: WO2018/221257
PCT Pub. Date: Dec. 6, 2018

(65) Prior Publication Data
US 2021/0128448 A1     May 6, 2021

(30) Foreign Application Priority Data
May 31, 2017 (JP) .............. JP2017-107525

(51) Int. Cl.
| | |
|---|---|
| *A61Q 5/12* | (2006.01) |
| *A61K 8/898* | (2006.01) |
| *A61K 8/34* | (2006.01) |
| *A61K 8/41* | (2006.01) |
| *A61K 8/58* | (2006.01) |
| *A61K 8/73* | (2006.01) |
| *A61K 8/81* | (2006.01) |
| *A61K 8/86* | (2006.01) |
| *A61K 8/88* | (2006.01) |
| *A61K 8/891* | (2006.01) |

(52) U.S. Cl.
CPC .............. *A61K 8/898* (2013.01); *A61K 8/345* (2013.01); *A61K 8/416* (2013.01); *A61K 8/585* (2013.01); *A61K 8/731* (2013.01); *A61K 8/817* (2013.01); *A61K 8/86* (2013.01); *A61K 8/88* (2013.01); *A61K 8/891* (2013.01); *A61Q 5/12* (2013.01); *A61K 2800/262* (2013.01); *A61K 2800/5426* (2013.01)

(58) Field of Classification Search
None
See application file for complete search history.

(56) References Cited

U.S. PATENT DOCUMENTS

| | | | |
|---|---|---|---|
| 2003/0108504 A1* | 6/2003 | Sako | ............... A61Q 5/12 424/70.12 |
| 2006/0171909 A1 | 8/2006 | Morrissey et al. | |
| 2013/0078209 A1 | 3/2013 | Yu et al. | |

FOREIGN PATENT DOCUMENTS

| | | |
|---|---|---|
| EP | 0972512 A1 | 1/2000 |
| EP | 1424065 A1 | 6/2004 |
| JP | 2000-034207 A | 2/2000 |
| JP | 2004-285047 A | 10/2004 |
| JP | 2008-169182 A | 7/2008 |
| JP | 2008-546807 A | 12/2008 |
| JP | 2009-132625 A | 6/2009 |
| WO | 2007/002566 A2 | 1/2007 |
| WO | 2011/056623 A1 | 5/2011 |

OTHER PUBLICATIONS

Translated Notice of Reasons for Rejection for counterpart Japanese Application No. 2017-107525, dated May 10, 2021.
International Search Report for counterpart Application No. PCT/JP2018/019210, dated Jul. 24, 2018.

* cited by examiner

*Primary Examiner* — Jyothsna A Venkat
(74) *Attorney, Agent, or Firm* — The Marbury Law Group, PLLC

(57) ABSTRACT

The present invention relates to a composition for treating keratin fibers, preferably hair, comprising: (a) at least one silicone oil in an amount of 20% by weight or more relative to the total weight of the composition; (b) water; and (c) at least one polyol in an amount of 10% by weight or more relative to the total weight of the composition, wherein the ratio of the amount of the (b) water/the amount of the (c) polyol is 3 or less. The composition according to the present invention can also provide keratin fibers such as hair with improved cosmetic effects such as smoothness (e.g., smooth combing even if the keratin fibers are wet, and smooth feeling to touch when the keratin fibers are dry), ease of running fingers through the keratin fibers even if the keratin fibers are wet, moist feeling even if the keratin fibers are dry, less stickiness (or less greasy) on hair when the keratin fibers are dry, and volume down control (therefore, it can be easy to style the shape of keratin fibers, due to anti-frizz properties of the composition according to the present invention).

20 Claims, No Drawings

COMPOSITION FOR KERATIN FIBERS

CROSS REFERENCE TO RELATED APPLICATION

This is a national stage application of PCT/JP2018/019210, filed internationally on May 11, 2018 which claims priority to Japanese Application No. 2017-107525, filed on May 31, 2017, both of which are incorporated by reference herein in their entirety.

TECHNICAL FIELD

The present invention relates to a composition for treating keratin fibers, preferably hair.

BACKGROUND ART

In the field of hair cosmetic treatments, leave-on type and leave-off type hair cosmetics are important sectors in the hair care category, and consumers use these hair cosmetics to provide hair with smoothness, moist feeling, volume control and the like. Recently, consumers are attracted by transparent hair cosmetics due to their clean appearance.

JP-A-2009-132625 discloses a transparent hair cosmetic composition including a specific cationic surfactant, an ethyleneoxide adduct to 1,2-dodecanediol, and water, wherein the amounts of these ingredient are limited to certain ranges. The hair cosmetic composition disclosed in JP-A-2009-132625 may include silicone. However, the amount of silicone is limited to up to 5% by weight relative to the total weight of the composition.

JP-T-2008-546807 also discloses a transparent or translucent hair cosmetic composition including a thickener, a cationic surfactant and/or a nonionic surfactant, a hydrophobicized amidesilicone copolyol, wherein the amounts of these ingredients are limited to certain ranges. The amount of the hydrophobicized amidesilicone copolyol is limited to up to about 10% by weight relative to the total weight of the composition.

DISCLOSURE OF INVENTION

An objective of the present invention is to provide a composition for keratin fibers such as hair which is transparent and stable, and can provide the keratin fibers with improved conditioning and manageability cosmetic effects such as smoothness, ease of running fingers through the hair, moist feeling, less stickiness on hair, and volume down control. The term "volume down" means that the spreading of keratin fibers is reduced or controlled, and therefore, the style of the keratin fibers can be well controlled.

The above objective can be achieved by a composition for treating keratin fibers, preferably hair, comprising:
(a) at least one silicone oil in an amount of 20% by weight or more relative to the total weight of the composition;
(b) water; and
(c) at least one polyol in an amount of 10% by weight or more relative to the total weight of the composition,
wherein
the weight ratio of the amount of the (b) water/the amount of the (c) polyol is 3 or less.

The amount of the (a) silicone oil in the composition may be 50% by weight or less, preferably 40% by weight or less, and more preferably 35% by weight or less, relative to the total weight of the composition.

The (a) silicone oil may comprise either at least one volatile silicone oil or at least one non-volatile silicone oil, or both of at least one volatile silicone oil and at least one non-volatile silicone oil.

The (a) silicone oil may comprise both at least one volatile silicone oil and at least one non-volatile silicone oil, and the amount of the non-volatile silicone oil is from 0.1 to 15% by weight, preferably from 0.5 to 10%, and more preferably from 1 to 5% by weight, relative to the total weight of the composition.

The volatile silicone oil may be selected from cyclic silicones.

The non-volatile silicone oil may be selected from polydimethylsiloxanes and organo-modified polydimethylsiloxanes.

The organo-modified polydimethylsiloxane may be selected from amodimethicones.

The amount of the (b) water in the composition may range from 1% to 40% by weight, preferably from 5% to 35% by weight, and more preferably from 10% to 30% by weight, relative to the total weight of the composition.

The (c) polyol may be selected from the group consisting of glycerin, ethyleneglycol, polyethyleneglycol, propyleneglycol, dipropyleneglycol, butyleneglycol, pentyleneglycol, hexyleneglycol and mixtures thereof.

The amount of the (c) polyol in the composition may be 50% by weight or less, preferably 45% by weight or less, and more preferably 40% by weight or less, relative to the total weight of the composition.

The weight ratio of the amount of the (b) water/the amount of the (c) polyol may be 0.1 or more, more preferably 0.2 or more, and more preferably 0.3 or more.

The composition according to the present invention may further comprise (d) at least one cationic polymer.

The composition according to the present invention may further comprise (e) at least one cationic surfactant.

The composition according to the present invention may be leave-on type or leave-off type.

The present invention also relates to a cosmetic process for keratin fibers, preferably hair, comprising the step of applying the composition according to the present invention to the keratin fibers.

BEST MODE FOR CARRYING OUT THE INVENTION

After diligent research, the inventors have discovered that it is possible to provide a composition for keratin fibers such as hair which is transparent and stable, and can provide the keratin fibers with improved conditioning and manageability cosmetic effects such as smoothness, ease of running fingers through the hair, moist feeling, less stickiness on hair, and volume down control.

Thus, the present invention mainly relates to a composition for treating keratin fibers, preferably hair, comprising:
(a) at least one silicone oil in an amount of 20% by weight or more relative to the total weight of the composition;
(b) water; and
(c) at least one polyol in an amount of 10% by weight or more relative to the total weight of the composition,
wherein
the weight ratio of the amount of the (b) water/the amount of the (c) polyol is 3 or less.

The composition according to the present invention includes a relatively higher amount of silicone oil(s) and polyol(s) as compared to conventional hair cosmetic compositions.

The composition according to the present invention is transparent and the transparent aspect of the present invention is stable over time, and therefore the composition according to the present invention can be attractive for consumers.

The composition according to the present invention can also provide keratin fibers such as hair with improved conditioning and manageability cosmetic effects such as smoothness (e.g., smooth combing even if the keratin fibers are wet, and smooth feeling to touch when the keratin fibers are dry), ease of running fingers through the keratin fibers even if the keratin fibers are wet, moist feeling even if the keratin fibers are dry, less stickiness (or less greasy) on hair when the keratin fibers are dry, and volume down control (therefore, it can be easy to style the shape of keratin fibers, due to anti-frizz properties of the composition according to the present invention).

Hereafter, the present invention will be described in a detailed manner.

[Composition]

One aspect of the present invention relates to a composition for treating keratin fibers, preferably hair, comprising:
(a) at least one silicone oil in an amount of 20% by weight or more relative to the total weight of the composition;
(b) water; and
(c) at least one polyol in an amount of 10% by weight or more relative to the total weight of the composition,
wherein
the weight ratio of the amount of the (b) water/the amount of the (c) polyol is 3 or less.

(Silicone Oil)

The composition according to the present invention comprises at least one (a) silicone oil. A single type of silicone oil may be used, or two or more different types of silicone oils may be used in combination.

Here, "silicone oil" means a silicone compound or substance which is in the form of a liquid or a paste at room temperature (25° C.) under atmospheric pressure (760 mmHg). As the silicone oils, those generally used in cosmetics may be used alone or in combination thereof.

Silicones or organopolysiloxanes are defined, for instance, by Walter NOLL in "Chemistry and Technology of Silicones" (1968), Academic Press. They may be volatile or non-volatile.

Thus, the (a) silicone oil(s) may be selected from volatile silicones, non-volatile silicones and mixtures thereof.

Thus, the (a) silicone oil may comprise either at least one volatile silicone oil or at least one non-volatile silicone oil, or both of at least one volatile silicone oil and at least one non-volatile silicone oil.

The volatile or non-volatile silicone may be selected from linear, branched, or cyclic silicones, optionally modified with at least one organo-functional moiety or group.

For example, the (a) silicone oil may be selected from the group consisting of polydialkylsiloxanes such as polydimethylsiloxanes (PDMS), polyalkylarylsiloxanes such as phenyltrimethicone, polydiarylsiloxanes, and organo-modified polysiloxanes comprising at least one organo-functional moiety or group chosen from poly(oxyalkylene) moieties or groups, amine or amide moieties or groups, alkoxy or alkoxyalkyl moieties or groups, hydroxyl or hydroxylated moieties or groups, acyloxy or acyloxyalkyl moieties or groups, carboxylic acid or carboxylate moieties or groups, hydroxyacylamino moieties or groups, acrylic moieties or groups, polyamine or polyamide moieties or groups, and oxazoline moieties.

If the (a) silicone oil(s) is/are volatile, the (a) silicone oil(s) may be chosen from those having a boiling point ranging from 60° C. to 260° C., for example:

(i) cyclic silicones such as polydialkylsiloxanes comprising from 3 to 7, for instance, from 4 to 6 silicon atoms. Non-limiting examples of such siloxanes include octamethylcyclotetrasiloxane marketed, for instance, under the trade name VOLATILE SILICONE® 7207 by UNION CARBIDE and SILBIONE® 70045 V2 by RHODIA, decamethylcyclopentasiloxane marketed under the trade name VOLATILE SILICONE® 7158 by UNION CARBIDE, and SILBIONE® 70045 V5 by RHODIA, KF-995 by SHIN ETSU, and dodecamethylcyclohexasiloxane (INCI: CYCLOHEXASILOXANE) marketed, for instance, under the trade name XIAMETER® PMX-246 and the trade name DC246 Fluid by Dow Corning, as well as mixtures thereof. Cyclomethicones may also be used, for example, those marketed under the references DC 244, DC 245, DC 344, DC 345, and DC 246 by DOW CORNING Cyclocopolymers of the dimethylsiloxane/methylalkylsiloxane type may also be used, such as SILICONE VOLATILE® FZ 3109 marketed by UNION CARBIDE, of formula

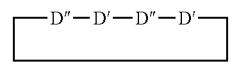

wherein:

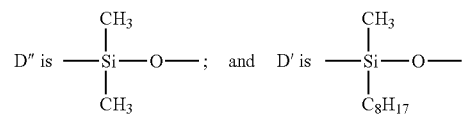

Combinations of cyclic silicones such as polydialkylsiloxanes with silicon derived organic compounds may also be used, such as an octamethylcyclotetrasiloxane and tetratrimethylsilylpentaerythritol (50/50) mixture, and an octamethylcyclotetrasiloxane and oxy-1,1'-(hexa-2,2,2',2',3,3'-trimethylsilyloxy) bis-neopentane mixture; and (ii) linear volatile polydialkylsiloxanes comprising from 2 to 9 silicon atoms. A non-limiting example of such a compound is decamethyltetrasiloxane marketed, for instance, under the trade name "SH-200" by TORAY SILICONE. Silicones belonging to this class are also described, for example, in Cosmetics and Toiletries, Vol. 91, January 76, P. 27-32—TODD & BYERS "Volatile Silicone Fluids for Cosmetics".

If the (a) silicone oil(s) is/are volatile, the (a) silicone oil(s) may be chosen from cyclic silicones.

On the other hand, the (a) silicone oil(s) may be chosen from non-volatile silicones, such as polydialkylsiloxanes, polyalkylarylsiloxanes, polydiarylsiloxanes, and organo-modified polysiloxanes as explained above.

According to one embodiment, the (a) silicone oil(s) may be chosen from non-volatile polydialkylsiloxanes, for example, polydimethylsiloxanes with trimethylsilyl end groups known under the trade name dimethicones. Non-limiting examples of commercial products corresponding to such polydialkylsiloxanes include:

SILBIONE® fluids of the series 47 and 70 047 and MIRASIL® fluids marketed by RHODIA, for example 70 047 fluid V 500 000;

fluids of the MIRASIL® series marketed by RHODIA;

fluids of the series 200 marketed by DOW CORNING such as DC200, with a viscosity of 60,000 mm$^2$/s;

XIAMETER® PMX-200 SILICONE FLUID 60000CS marketed by Dow Corning; VISCASIL® fluids of GENERAL ELECTRIC and some fluids of the SF series (e.g., SF 96 and SF 18) of GENERAL ELECTRIC; and the fluid marketed under the reference DC 1664 by DOW CORNING.

Products marketed under the trade names "ABIL Wax® 9800 and 9801" by GOLDSCHMIDT belonging to this class of polydialkylsiloxanes, which are polydialkyl ($C_1$-$C_{20}$) siloxanes, may also be used.

Polyalkylarylsiloxanes may be chosen from polydimethyl/methylphenylsiloxanes, linear and/or branched polydimethyl/diphenyl siloxanes.

Non-limiting examples of such polyalkylarylsiloxanes include the products marketed under the following trade names:

SILBIONE® fluids of the 70 641 series from RHODIA; RHODORSIL® fluids of the 70 633 and 763 series from RHODIA;

phenyltrimethicone fluid marketed under the reference DOW CORNING 556 COSMETIC GRADE FLUID by DOW CORNING;

PK series silicones from BAYER, for example, the PK20 product;

PN, PH series silicones from BAYER. for example, the PN1000 and PH000 products; and some SF series fluids from GENERAL ELECTRIC, such as SF 1023, SF 1154, SF 1250, and SF 1265.

Organo-modified silicones which may be used according to the present invention include, but are not limited to, silicones such as those previously defined and comprising within their structure at least one organo-functional moiety or group linked directly or by means of a hydrocarbon group.

Organo-modified silicones may include, for example, polyorganosiloxanes comprising: polyethyleneoxy and/or polypropyleneoxy moieties optionally comprising $C_6$-$C_{24}$ alkyl moieties, such as products called dimethicone copolyols marketed by DOW CORNING under the trade name DC 1248 and under the trade name DC Q2-5220 and SILWET® L 722, L 7500, L 77, and L 711 fluids marketed by UNION CARBIDE, as well as PEG12 dimethicone marked under the trade name XIAMETER® OFX-0193 FLUID by DOW CORNING, and ($C_{12}$)alkyl-methicone copolyol marketed by DOW CORNING under the trade name Q2 5200; optionally substituted amine moieties, for example, the products marketed under the trade name GP 4 Silicone Fluid and GP 7100 by GENESEE and the products marketed under the trade names Q2 8220 and DOW CORNING 929 and 939 by DOW CORNING. Substituted amine moieties may be chosen, for example, from amino $C_1$-$C_4$ alkyl moieties.

Aminosilicones or amodimethicones may have additional $C_1$-$C_4$ alkoxy functional groups, such as those corresponding to the WACKER BELSIL ADM LOG 1 product.

Aminosilicones or amodimethicones may have at least one, preferably two, additional alkyl group(s) such as $C_{12}$-$C_{20}$, preferably $C_{14}$-$C_{18}$, and more preferably $C_{16}$-$C_{18}$ alkyl groups, preferably at the terminal(s) of the molecular chain thereof, such as bis-cetearylamodimethicone, marketed under the trade name "Silsoft Ax" by Momentive Performance Materials;

alkoxylated moieties, such as the product marketed under the trade name "SILICONE COPOLYMER F-755" by SWS SILICONES and ABIL WAX® 2428, 2434, and 2440 by GOLDSCHMIDT;

hydroxylated moieties, such as hydroxyalkyl function-containing polyorganosiloxanes described, for instance, in French Patent Application No. FR-A-85 163 34;

acyloxyalkyl moieties, for example, the polyorganosiloxanes described in U.S. Pat. No. 4,957,732;

anionic moieties of the carboxylic acid type, for example, the products described in European Patent No. 0 186 507, marketed by CHISSO CORPORATION, and carboxylic alkyl anionic moieties, such as those present in the X-22-3701E product marketed by SHIN-ETSU; 2-hydroxyalkyl sulfonate; and 2-hydroxyalkyl thiosulfate such as the products marketed by GOLDSCHMIDT under the trade names <<ABIL® S201>> and <<ABIL® S255>>; hydroxyacylamino moieties, such as the polyorganosiloxanes described in European Patent Application No. 0 342 834. A non-limiting example of a corresponding commercial product is the Q2-8413 product marketed by DOW CORNING;

acrylic moieties, such as the products marketed under the names VS80 and VS70 by 3M; polyamine moieties, and oxazoline moieties

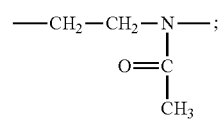

silicones that may be used according to the present invention may comprise 1 or 2 oxazoline groups; for example, poly(2-methyl oxazoline-b-dimethyl siloxane-b-2-methyl oxazoline) and poly(2-ethyl-2-oxazoline-dimethyl siloxane). The products marketed by KAO under the references OX-40, OS-51, OS-96, and OS-88 may also be used.

Polydimethylsiloxanes with dimethylsilanol end groups may also be used, for example, those sold under the trade name dimethiconol (CTFA), such as fluids of the 48 series marketed by RHODIA.

If the (a) silicone oil(s) is/are non-volatile, the (a) silicone oil(s) may be chosen from polydimethylsiloxanes and organo-modified polydimethylsiloxanes. The organo-modified polydimethylsiloxane may be selected from amodimethicones. The viscosity of the polydimethylsiloxane or the organo-modified polydimethylsiloxane may be from 1,000,000 cst to 20,000,000 cst.

It may be preferable that the (a) silicone oil be selected from volatile or non-volatile silicone oils, such as volatile or non-volatile polydimethylsiloxanes (PDMS) containing a linear or cyclic silicone chain, that are liquid or pasty at ambient temperature, in particular cyclopolydimethylsiloxanes (cyclomethicones) such as cyclopentasiloxane and cyclohexasiloxane; polydimethylsiloxanes containing alkyl, alkoxy, or phenyl groups that are pendent and/or at the end(s) of the silicone chain, which groups have from 1 to 24 carbon atoms; phenyl silicones such as phenyltrimethicones, phenyldimethicones, phenyltrimethylsiloxydiphenylsiloxanes, diphenyldimethicones, diphenylmethyldiphenyltrisiloxanes, 2-phenylethyltrimethyl siloxysilicates, and polymethylphenylsiloxanes; and organo-modified silicones such as dimethiconol, dimethicone copolyol (e.g., PEG12 dimethicone) and amodimethicone (e.g., bis-cetearylamodimethicone).

It is possible to use a combination of at least one volatile silicone and at least one non-volatile silicone, as the (a) silicone oil. Non-limiting examples of such combinations include a mixture of cyclopentasiloxane and dimethiconol, marketed, for instance, under the trade name Xiameter PMX-1501 Fluid by Dow Corning.

The amount of the (a) silicone oil in the composition according to the present invention is 20% by weight or more, preferably 23% by weight or more, and more preferably 25% by weight or more, relative to the total weight of the composition.

On the other hand, the amount of the (a) silicone oil in the composition according to the present invention may be 50% by weight or less, preferably 40% by weight or less, and more preferably 35% by weight or less, relative to the total weight of the composition.

Accordingly, the amount of the (a) silicone in the composition according to the present invention may range from 20% to 50% by weight, preferably from 23% to 40% by weight, and more preferably from 25% to 35% by weight, relative to the total weight of the composition.

If the (a) silicone oil comprises both at least one volatile silicone oil and at least one non-volatile silicone oil, the amount of the non-volatile silicone oil may be from 0.1% to 15% by weight, preferably from 0.5% to 10%, and more preferably from 1% to 5% by weight, relative to the total weight of the composition.

(Water)

The composition according to the present invention comprises (b) water.

The amount of the (b) water in the composition according to the present invention may be 1% by weight or more, preferably 5% by weight or more, and more preferably 10% by weight or more, relative to the total weight of the composition.

The amount of the (b) water in the composition according to the present invention may be 40% by weight or less, preferably 35% by weight or less, and more preferably 30% by weight or less, relative to the total weight of the composition.

Thus, the amount of the (b) water in the composition according to the present invention may range from 1% to 40% by weight, preferably from 5% to 35% by weight, and more preferably from 10% to 30% by weight, relative to the total weight of the composition.

(Polyol)

The composition according to the present invention comprises (c) at least one polyol. A single type of polyol may be used, or two or more different types of polyols may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The (c) polyol may be a $C_{2-12}$ polyol, preferably a $C_{2-9}$ polyol, comprising at least 2 hydroxy groups, and preferably 2 to 5 hydroxy groups.

The (c) polyol may be a natural or synthetic polyol. The (c) polyol may have a linear, branched or cyclic molecular structure.

The (c) polyol may be selected from glycerins and derivatives thereof, and glycols and derivatives thereof. The polyol may be selected from the group consisting of glycerin, diglycerin, polyglycerin, ethyleneglycol, diethyleneglycol, polyethyleneglycol, propyleneglycol, dipropyleneglycol, polypropyleneglycol, butyleneglycol, pentyleneglycol, hexyleneglycol, 1,2-propanediol, 1,3-propanediol, and 1,5-pentanediol.

It may be preferable that the (c) polyol have 3 or more carbon atoms, and be selected from the group consisting of glycerin, ethyleneglycol, polyethyleneglycol, propyleneglycol, dipropyleneglycol, butyleneglycol, pentyleneglycol, hexyleneglycol and mixtures thereof.

It may be more preferable that the (c) polyol have a refractive index of 1.4 or more.

The polyol may be an alkylene oxide derivative represented by the following formula (I):

$$Z-\{O(AO)_l(EO)_m-(BO)_nH\}_a \qquad (I)$$

wherein

Z denotes a residue obtained by removing hydroxyl group(s) from a compound having 3 to 9 hydroxyl groups;

AO denotes an oxyalkylene group having 3 to 4 carbon atoms;

EO denotes an oxyethylene group;

BO denotes an oxyalkylene group having 4 carbon atoms;

a denotes 3 to 9;

l, m, and n denote the average addition mole numbers of AO, EO and BO, respectively, and $1 \leq l \leq 50$, $1 \leq m \leq 50$ and $0.5 \leq n \leq 5$;

a weight ratio of AO to EO (AO/EO) ranges from 1/5 to 5/1; and

AO and EO may have been added randomly or in the form of blocks.

The aforementioned alkylene oxide derivatives may be a single type thereof, or a mixture of plural types thereof.

In the alkylene oxide derivative represented by formula (I), Z denotes a residue obtained by removing hydroxyl groups from a compound having 3 to 9 hydroxyl groups, and a denotes the number of hydroxyl groups of the compound and is 3 to 9. As examples of compounds having 3 to 9 hydroxyl groups, mention may be made of, for example, in the case of a=3, glycerin, and trimethylolpropane; in the case of a=4, erythritol, pentaerythritol, sorbitol, alkylglycosides, and diglycerin; in the case of a=5, xylitol; in the case of a=6, dipentaerythritol, sorbitol, and inositol; in the case of a=8, sucrose, and trehalose; in the case of a=9, maltitol; mixtures thereof; and the like. Preferably, Z denotes a residue obtained by removing hydroxyl group(s) from a compound having 3 to 6 hydroxyl groups, and a satisfies $3 \leq a \leq 6$. As the compound having 3 to 9 hydroxyl groups, glycerin or trimethylolpropane is preferable, and in particular, glycerin is preferable. In the case of $a \leq 2$, poor compatibility with oil components such as fats and oils may be exhibited, and blending stability in an oil-based formulation may tend to be impaired. In the case of $10 \leq a$, stickiness may occur.

AO denotes an oxyalkylene group having 3 to 4 carbon atoms. As examples thereof, mention may be made of, for example, an oxypropylene group, an oxybutylene group (an oxy-n-butylene group, an oxyisobutylene group, or an oxy-t-butylene group), an oxytrimethylene group, an oxytetramethylene group, and the like. The oxypropylene group and oxybutylene group are preferable, and the oxypropylene group is more preferable.

l denotes the average addition mole number of AO, and satisfies 1≤l≤50, and preferably 2≤l≤20. m denotes the average addition mole number of EO, and satisfies 1≤m≤50, and preferably 2≤m≤20. If l is 0, stickiness may occur. On the other hand, if l exceeds 50, moisturizing effects may be decreased. In addition, if m is 0, moisturizing effects may be decreased. On the other hand, if m exceeds 50, stickiness may occur.

The weight ratio of AO to EO (AO/EO) ranges from 1/5 to 5/1, and preferably ranges from 1/4 to 4/1. If AO/EO is below 1/5, stickiness may occur. On the other hand, if AO/EO exceeds 5/1, the moisturizing sensation may be decreased. The order of adding AO and EO is not particularly specified. AO and EO can be added randomly or in the form of blocks. In order to obtain superior effects of preventing skin roughness, AO and EO are preferably added randomly.

BO denotes an oxyalkylene group having 4 carbon atoms. As examples thereof, mention may be made of, for example, an oxybutylene group (an oxy-n-butylene group, an oxy-isobutylene group, or an oxy-t-butylene group), an oxytetramethylene group, and the like. The oxybutylene group is preferable.

n denotes the average addition mole number of BO, and satisfies 0.5<n≤5, preferably 0.8≤n≤3, and more preferably 1≤n≤3. If n is below 0.5, stickiness may occur. On the other hand, if n exceeds 5, moisturizing effects may be decreased. In formula (I), it is necessary that (BO)$_n$ bonds to the terminal hydrogen atom.

The alkylene oxide derivatives represented by formula (I) can be produced by means of known methods. For example, the alkylene oxide derivatives represented by formula (I) can be obtained by additive-polymerizing ethylene oxide and an alkylene oxide having 3 to 4 carbon atoms to a compound having 3 to 9 hydroxyl groups, and subsequently reacting with an alkylene oxide having 4 carbon atoms. When additive-polymerizing ethylene oxide and an alkylene oxide having 3 to 4 carbon atoms to a compound having 3 to 9 hydroxyl groups, the ethylene oxide and alkylene oxide may be polymerized randomly or in the form of blocks.

Among the alkylene oxide derivatives represented by formula (I), preferable examples of the aforementioned alkylene oxide derivatives include, for example, an alkylene oxide derivative (polyoxybutylene polyoxyethylene polyoxypropylene glycerol) represented by formula (II). shown below:

Gly-[O(PO)$_s$(EO)$_t$—(BO)$_u$H]$_3$     (II)

wherein
Gly denotes a residue obtained by removing hydroxyl groups from glycerin;
PO denotes an oxypropylene group;
EO denotes an oxyethylene group;
s and t denote the average addition mole numbers of PO and EO, respectively, and have a value ranging from 1 to 50;
the weight ratio of PO to EO (PO/EO) ranges from 1/5 to 5/1;
BO denotes an oxyalkylene group having 4 carbon atoms; and
u denotes the average addition mole number of BO, and ranges from 0.5 to 5.

The aforementioned alkylene oxide derivative represented by formula (II) can be obtained by adding propylene oxide and ethylene oxide to glycerin, in the ratio of 3 to 150 mole equivalents of each of propylene oxide and ethylene oxide with respect to glycerin, and subsequently, adding the alkylene oxide having 4 carbon atoms in the ratio of 1.5 to 15 mole equivalents thereof with respect to glycerin.

In the case of adding the aforementioned alkylene oxides to glycerin, the addition reactions are carried out with an alkali catalyst, a phase transfer catalyst, a Lewis acid catalyst, or the like. In general, an alkali catalyst such as potassium hydroxide is preferably employed.

Among the alkylene oxide derivatives represented by formula (I), more preferable derivatives are obtained by adding 6 to 10 mol of ethylene oxide and 3 to 7 mol of propylene oxide to glycerin, and subsequently, adding 2 to 4 mol of butylene oxide.

Among the alkylene oxide derivatives represented by formula (I), a further more preferable derivative is polyoxybutylene polyoxyethylene polyoxypropylene glycerol, which is obtained by adding 8 mol of ethylene oxide and 5 mol of propylene oxide to glycerin, and subsequently, adding 3 mol of butylene oxide, and which has an INCI name of PEG/PPG/polybutylene glycol-8/5/3 glycerin. PEG/PPG/polybutylene glycol-8/5/3 glycerin is commercially available under the trade name of WILBRIDE S-753 from NOF Corporation.

The amount of the (c) polyol(s) in the composition according to the present invention may be 50% by weight or less, preferably 45% by weight or less, and more preferably 40% by weight or less, relative to the total weight of the composition.

On the other hand, the amount of the (c) polyol(s) in the composition according to the present invention is 10% by weight or more, preferably 20% by weight or more, and more preferably from 30% by weight or more, relative to the total weight of the composition.

Accordingly, the amount of the (c) polyol(s) in the composition according to the present invention may range from 10% to 50% by weight, preferably from 20% to 45% by weight, and more preferably from 30% to 40% by weight, relative to the total weight of the composition.

According to the present invention, the weight ratio of the amount of the (b) water/the amount of the (c) polyol is 3 or less, preferably 2 or less, more preferably 1 or less, and even more preferably 0.8 or less.

On the other hand, the weight ratio of the amount of the (b) water/the amount of the (c) polyol may be 0.1 or more, preferably 0.2 or more, more preferably 0.3 or more, and even more preferably 0.4 or more.

Accordingly, the weight ratio of the amount of the (b) water/the amount of the (c) polyol may be from 0.1 to 3, preferably from 0.2 to 2, more preferably from 0.3 to 1, and even more preferably from 0.4 to 0.8.

(Cationic Polymer)

The composition according to the present invention may comprise (d) at least one cationic polymer. A single type of cationic polymer may be used, but two or more different types of cationic polymers may be used in combination.

It should be noted that, for the purposes of the present invention, the term "cationic polymer" denotes any polymer containing cationic groups and/or groups that may be ionized into cationic groups.

Such polymers may be chosen from those already known per se as improving the cosmetic properties of the hair, i.e., especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between approximately 500 and approximately $5 \times 10^6$ and preferably between approximately 103 and approximately $3 \times 10^6$.

Among the cationic polymers that may be mentioned more particularly are polymers of the polyamine, polyamino amide and polyquaternary ammonium type.

These are known products. They are described in particular in French patents 2 505 348 and 2 542 997. Among the said polymers, mention may be made of the following.

(1) homopolymers or copolymers derived from acrylic or methacrylic esters or amides and comprising at least one of the units of formula (I), (II), (III) or (IV) below:

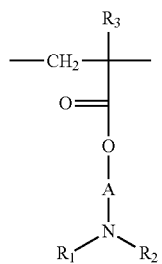
(I)

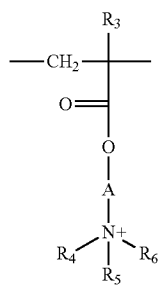
(II)

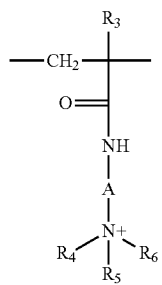
(III)

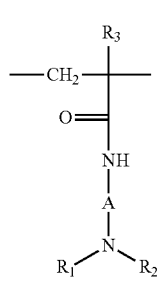
(IV)

in which $R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl; and X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinyl-caprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company BASF, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, and vinylpyrrolidone/methacrylamidopropyldimethylamine copolymers sold in particular under the name Styleze CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French patent 1 492 597, and in particular the polymers sold under the names "JR" (JR 400, JR 125, JR 30M) or "LR" (LR 400, LR 30M) by the company Amerchol. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described especially in U.S. Pat. No. 4,131,576, such as hydroxyalkylcelluloses, for instance hydroxymethyl-, hydroxyethyl- or hydroxypropylcelluloses grafted especially with a methacryloylethyl-trimethylammonium, methacrylamidopropyltrimethylammonium or dimethyldiallylammonium salt.

The commercial products corresponding to this definition are more particularly the products sold under the name Celquat L 200 and Celquat H 100 by the company Akzo Nobel.

(4) The cationic guar gums described more particularly in U.S. Pat. No. 3,589,578 and 4 031307, such as guar gums containing trialkylammonium cationic groups. Use is made, for example, of guar gums modified with a salt (e.g., chloride) of 2,3-epoxypropyltrimethylammonium. Mention may be made of guar hydroxypropyltrimonium chloride and hydroxypropyl guar hydroxypropyl trimonium chloride, such as those sold especially under the trade names Jaguar C13S, Jaguar C14S, Jaguar C17 and Jaguar C162 by the company Solvay.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) Cyclopolymers of alkyldiallylamine or of dialkyldiallylammonium, such as the homopolymers or copolymers containing, as a main constituent of the chain, units corresponding to formula (V) or (VI):

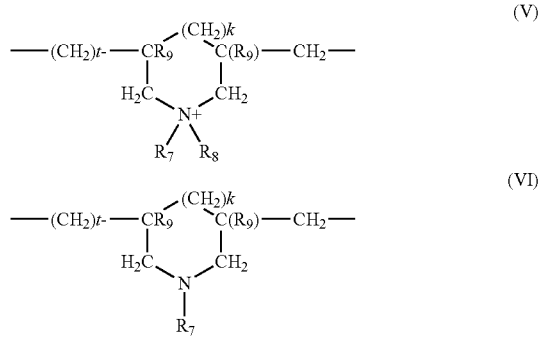

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 6 carbon atoms, a hydroxyalkyl group in which the alkyl group preferably has 1 to 5 carbon atoms, a lower ($C_1$-$C_4$) amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; and Y is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat 100" by the company Nalco (and its homologues of low weight-average molecular mass) and the copolymers of diallyldimethylammonium chloride and of acrylamide, sold under the name "Merquat 550".

(8) The quaternary diammonium polymer containing repeating units corresponding to the formula:

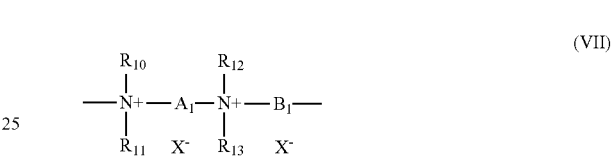

in which formula (VII):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —($CH_2$)$_n$—C-D-C—($CH_2$)$_n$— in which D denotes:

i) a glycol residue of formula: —O—Z—O—, where Z denotes a linear or branched hydrocarbon-based radical or a group corresponding to one of the following formulae:

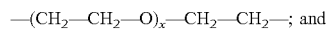

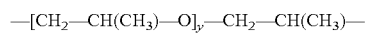

where x and y denote an integer from 1 to 4, representing a defined and unique degree of polymerization or any number from 1 to 4 representing an average degree of polymerization;

ii) a bis-secondary diamine residue such as a piperazine derivative;

iii) a bis-primary diamine residue of formula —NH—Y—NH—, where Y denotes a linear or branched hydrocarbon-based radical, or alternatively the divalent radical —CH$_2$—CH$_2$—S—S—CH$_2$—CH$_2$—; or iv) a ureylene group of formula —NH—CO—NH—.

Preferably, X$^-$ is an anion such as chloride or bromide.

These polymers generally have a number-average molecular mass of between 1000 and 100000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the following formula (VIII):

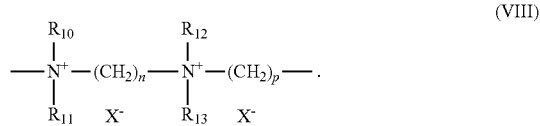

(VIII)

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and X$^-$ is an anion derived from a mineral or organic acid.

One particularly preferred compound of formula (VIII) is that for which $R_{10}$, $R_{11}$ $R_{12}$ and $R_{13}$ represent a methyl group, n=3, p=6 and X=Cl, which is called Hexadimethrine chloride according to the INCI(CTFA) nomenclature.

(9) Polyamines such as Polyquart H sold by Cognis, which is given under the reference name "Polyethylene glycol (15) tallow polyamine" in the CTFA dictionary.

(10) Crosslinked methacryloyloxy(C$_1$-C$_4$)alkyltri(C$_1$-C$_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name "Salcare® SC 92" by the company BASF. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

(11) Other cationic polymers which can be used in the context of the present invention are polyalkyleneimines, in particular polyethyleneimines, polymers containing vinylpyridine or vinylpyridinium units, condensates of polyamines and of epichlorohydrin, quaternary polyureylenes and chitin derivatives.

It is preferable that the cationic polymer be a polyquaternium polymer or a polymeric quaternary ammonium salt.

Polymeric quaternary ammonium salts are cationic polymers comprising at least one quaternized nitrogen atom. Mention may in particular be made, as polymeric quaternary ammonium salts, of the Polyquaternium products (CTFA name), which contribute mainly to the quality of foam and feeling of the skin after use, in particular the feeling of the skin after use. These polymers can preferably be chosen from the following polymers:

Polyquaternium-5, such as the product Merquat 5 sold by Nalco;

Polyquaternium-6, such as the product Salcare SC 30 sold by BASF and the product Merquat 100 sold by Nalco;

Polyquaternium-7, such as the products Merquat S, Merquat 2200, Merquat 7SPR, and Merquat 550 sold by Nalco and the product Salcare SC 10 sold by BASF;

Polyquaternium-10, such as the product Polymer JR400 sold by Amerchol;

Polyquaternium-11, such as the products Gafquat 755, Gafquat 755N and Gafquat 734 sold by ISP;

Polyquaternium-15, such as the product Rohagit KF 720 F sold by Röhm;

Polyquaternium-16, such as the products Luviquat FC905, Luviquat FC370, Luviquat HM552 and Luviquat FC550 sold by BASF;

Polyquaternium-22, such as the product Merquat 295 sold by Nalco;

Polyquaternium-28, such as the product Styleze CC10 sold by ISP;

Polyquaternium-44, such as the product Luviquat Care sold by BASF;

Polyquaternium-46, such as the product Luviquat Hold sold by BASF; and

Polyquaternium-47, such as the product Merquat 2001 sold by Nalco.

Preferably, the (d) cationic polymer may be chosen from, Polyquaternium-22, Polyquaternium-47 and their mixtures.

The amount of the (d) cationic polymer(s) may be 20% by weight or less, preferably 10% by weight or less, and more preferably 5% by weight or less, relative to the total weight of the composition according to the present invention, with the proviso that the amount of the (d) cationic polymer(s) is not zero. The amount of the (d) cationic polymer(s) may be 0.01% by weight or more, preferably 0.1% by weight or more, and more preferably from 1% by weight or more, relative to the total weight of the composition according to the present invention.

The composition according to the present invention may contain the (d) cationic polymer(s) in an amount of from 0.01% to 20% by weight, preferably from 0.1 to 10% by weight, and more preferably 1 to 5% by weight, relative to the total weight of the composition.

(Cationic Surfactant)

The composition according to the present invention may comprise (e) at least one cationic surfactant. A single type of cationic surfactant may be used, but two or more different types of cationic surfactants may be used in combination.

The (e) cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to:

those of general formula (V) below:

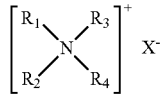

wherein $R_1$, $R_2$, $R_3$, and $R_4$, which may be identical or different, are chosen from linear and branched aliphatic radicals comprising from 1 to 30 carbon atoms and optionally comprising heteroatoms such as oxygen, nitrogen, sulfur and halogens. The aliphatic radicals may be chosen, for example, from alkyl, alkoxy, $C_2$-$C_6$ polyoxyalkylene, alkylamide, ($C_{12}$-$C_{22}$)alkylamido($C_2$-$C_6$)alkyl, ($C_{12}$-$C_{22}$)alkylacetate and hydroxyalkyl radicals; and aromatic radicals such as aryl and alkylaryl; and $X^-$ is chosen from halides, phosphates, acetates, lactates, ($C_2$-$C_6$) alkyl sulfates and alkyl- or alkylaryl-sulfonates; quaternary ammonium salts of imidazoline, for instance those of formula (VI) below:

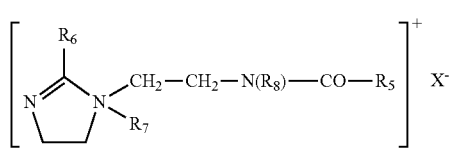

wherein:

$R_5$ is chosen from alkenyl and alkyl radicals comprising from 8 to 30 carbon atoms, for example fatty acid derivatives of tallow or of coconut;

$R_6$ is chosen from hydrogen, $C_1$-$C_4$ alkyl radicals, and alkenyl and alkyl radicals comprising from 8 to 30 carbon atoms;

$R_7$ is chosen from $C_1$-$C_4$ alkyl radicals;

$R_8$ is chosen from hydrogen and $C_1$-$C_4$ alkyl radicals; and $X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco;

diquaternary ammonium salts of formula (VII):

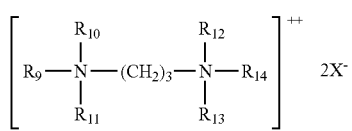

wherein:

$R_9$ is chosen from aliphatic radicals comprising from 16 to 30 carbon atoms;

$R_{10}$, $R_{11}$, $R_{12}$, $R_{13}$, and $R_{14}$, which may be identical or different, are chosen from hydrogen and alkyl radicals comprising from 1 to 4 carbon atoms; and $X^-$ is chosen from halides, acetates, phosphates, nitrates, ethyl sulfates, and methyl sulfates.

An example of one such diquaternary ammonium salt is propanetallowdiammonium dichloride; and quaternary ammonium salts comprising at least one ester function, such as those of formula (VIII) below:

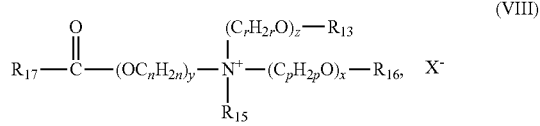

wherein:

$R_{15}$ is chosen from $C_1$-$C_6$ alkyl radicals and $C_1$-$C_6$ hydroxyalkyl and dihydroxyalkyl radicals;

$R_{16}$ is chosen from:

the radical blow:

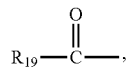

linear and branched, saturated and unsaturated $C_{1-C22}$ hydrocarbon-based radicals $R_{20}$, and hydrogen, $R_{18}$ is chosen from:

the radical below:

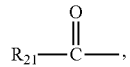

linear and branched, saturated and unsaturated $C_1$-$C_6$ hydrocarbon-based radicals $R_{22}$, and hydrogen, $R_{17}$, $R_{19}$, and $R_{21}$, which may be identical or different, are chosen from linear and branched, saturated and unsaturated, $C_7$-$C_{21}$, hydrocarbon-based radicals;

r, n, and p, which may be identical or different, are chosen from integers ranging from 2 to 6;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{16}$ denotes $R_{20}$, and that when z is 0, $R_{18}$ denotes $R_{22}$. $R_{15}$ may be chosen from linear and branched alkyl radicals. In one embodiment, $R_{15}$ is chosen from linear alkyl radicals. In another embodiment, $R_{15}$ is chosen from methyl, ethyl, hydroxyethyl, and dihydroxypropyl radicals, for example methyl and ethyl radicals. In one embodiment, the sum x+y+z ranges from 1 to 10. When $R_{16}$ is a hydrocarbon-based radical $R_{20}$, it may be long and comprise from 12 to 22 carbon atoms, or short and comprise from 1 to 3 carbon atoms. When $R_{18}$ is a hydrocarbon-based radical $R_{22}$, it may comprise, for example, from 1 to 3 carbon atoms. By way of a non-limiting example, in one embodiment, $R_{17}$, $R_{19}$, and $R_{21}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, n and p, which may be identical or different, are equal to 2 or 3, for example equal to 2. The anion $X^-$ may be chosen from, for example, halides, such as chloride, bromide, and iodide; and C1-C4 alkyl sulfates, such as methyl sulfate. However, methanesulfonate, phosphate, nitrate, tosylate, an anion derived from an organic acid, such as acetate and lactate, and any other anion that is compatible with the ammonium comprising an ester function, are other non-limiting examples of anions that may be used according to the invention. In one embodiment, the anion $X^-$ is chosen from chloride and methyl sulfate.

In another embodiment, the ammonium salts of formula (VIII) may be used, wherein:
$R_{15}$ is chosen from methyl and ethyl radicals,
x and y are equal to 1;
z is equal to 0 or 1;
r, n and p are equal to 2;
$R_{16}$ is chosen from:
the radical below:

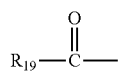

methyl, ethyl, and $C_{14}$-$C_{22}$ hydrocarbon-based radicals, hydrogen;
$R_{18}$ is chosen from:
the radical below:

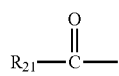

hydrogen;
$R_{17}$, $R_{19}$, and $R_{21}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (VIII) that may be mentioned include salts, for example chloride and methyl sulfate, of diacyloxyethyl-dimethylammonium, of diacyloxyethyl-hydroxyethyl-methylamm-onium, of monoacyloxyethyl-dihydroxyethyl-methylammonium, of triacyloxyethyl-methylammonium, of monoacyloxyethyl-hydroxyethyl-dimethyl-ammonium, and mixtures thereof. In one embodiment, the acyl radicals may comprise from 14 to 18 carbon atoms, and may be derived, for example, from a plant oil, for instance palm oil and sunflower oil. When the compound comprises several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

The compositions according to the invention may comprise, for example, a mixture of quaternary ammonium mono-, di- and triester salts with a weight majority of diester salts.

A non-limiting example of a mixture of ammonium salts that may be used in the compositions according to the invention is that comprising from 15% to 30% by weight of acyloxyethyl-dihydroxyethyl-methylammonium methyl sulfate, from 45% to 60% by weight of diacyloxyethyl-hydroxyethyl-methylammonium methyl sulfate, and from 15% to 30% by weight of triacyloxyethyl-methylammonium methyl sulfate, the acyl radicals of all these compounds comprising from 14 to 18 carbon atoms and being derived from optionally partially hydrogenated palm oil.

Other non-limiting examples of ammonium salts that may be used in the compositions according to the invention include the ammonium salts comprising at least one ester function described in U.S. Pat. Nos. 4,874,554 and 4,137,180.

Among the quaternary ammonium salts mentioned above that may be used in compositions according to the invention include, but are not limited to, those corresponding to formula (V), for example tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate)ammonium chloride, sold under the name "Ceraphyl® 70" by the company Van Dyk.

According to one embodiment, the at least one cationic surfactant that may be used in the compositions of the invention is chosen from quaternary ammonium salts, for example from behenyltrimethylammonium chloride, cetyltrimethylammonium chloride (cetrimonium chloride), Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

The amount of the (e) cationic surfactant(s) may be 20% by weight or less, preferably 15% by weight or less, and more preferably 10% by weight or less, relative to the total weight of the composition according to the present invention, with the proviso that the amount of the (e) cationic surfactant(s) is not zero. The amount of the (e) cationic surfactant(s) may be 0.01% by weight or more, preferably 0.1% by weight or more, and more preferably from 1% by weight or more, relative to the total weight of the composition according to the present invention.

The composition according to the present invention may contain the (e) cationic surfactant (s) in an amount of from 0.01% to 20% by weight, preferably from 0.1 to 15% by weight, and more preferably 1 to 10% by weight, relative to the total weight of the composition.

(Other Ingredients)

The composition according to the present invention may also include at least one optional or additional ingredient.

The optional or additional ingredient(s) may be selected from the group consisting of anionic, nonionic or amphoteric polymers; anionic, nonionic or amphoteric surfactants; organic or inorganic UV filters; peptides and derivatives thereof; protein hydrolyzates; swelling agents and penetrating agents; agents for combating hair loss; anti-dandruff agents; natural or synthetic thickeners for water or oils; suspending agents; sequestering agents; dyes; sunscreen agents; vitamins or provitamins; fragrances; preservatives, co-preservatives, stabilizers; and mixtures thereof.

The amount of the optional or additional ingredient(s) is not limited, but may be from 0.01% to 30% by weight, preferably from 0.1% to 20% by weight, and more preferably from 1% to 10% by weight, relative to the total weight of the composition according to the present invention.

[Preparation]

The composition according to the present invention can be prepared by mixing the essential ingredient(s) as explained above, and optional ingredient(s), if necessary, as explained above.

The method and means to mix the above essential and optional ingredients are not limited. Any conventional method and means can be used to mix the above essential and optional ingredients to prepare the composition according to the present invention.

[Form]

The composition according to the present invention may be leave-on type or leave-off type, preferably leave-on type.

[Process]

The composition according to the present invention may preferably be used as a cosmetic composition. The cosmetic composition may be used for treating keratin fibers. The keratin fibers may be hair, eyebrows, eyelashes and the like.

In particular, the composition according to the present invention may be intended for application onto keratin fibers such as hair. Thus, the composition according to the present invention can be used for a cosmetic process for keratin fibers.

The present invention also relates to a process for keratin fibers, preferably hair, comprising the step of applying the composition according to the present invention to the keratin fibers.

The keratin fibers to which the composition according to the present invention has been applied can be left for an appropriate time which is required to treat the keratin fibers. The time length for each treatment is not limited, but it may be from 1 minute to 10 minutes, preferably from 1 minute to 5 minutes, and more preferably from 1 minute to 3 minutes. Thus, for example, the total time for the treatments according to the present invention may be from 3 to 30 minutes, preferably from 3 to 15 minutes, and more preferably from 3 minutes to 10 minutes.

The keratin fibers may be treated at room temperature. Alternatively, the keratin fibers can be heated at 15° C. to 45° C., preferably 20° C. to 40° C., more preferably 25° C. to 35° C., and even more preferably 27° C. to 35° C., before and/or during and/or after the step of applying the composition according to the present invention onto the keratin fibers.

The keratin fibers to which the composition according to the present invention has been applied may or may not be rinsed.

The process, preferably cosmetic process, according to the present invention can provide keratin fibers such as hair with improved conditioning and manageability cosmetic effects such as smoothness (e.g., smooth combing even if the keratin fibers are wet, and smooth feeling to touch when the keratin fibers are dry), ease of running fingers through the keratin fibers even if the keratin fibers are wet, moist feeling even if the keratin fibers are dry, less stickiness (or less greasy) on hair when the keratin fibers are dry, and volume down control (therefore, it can be easy to style the shape of keratin fibers, due to anti-frizz properties of the composition according to the present invention). The term "volume down" means that spreading of keratin fibers is reduced or controlled, and therefore, the style of the keratin fibers can be well controlled.

In particular, the process according to the present invention can provide keratin fibers such as hair with higher level of smoothness, moisturizing, volume control and the like, as well as less stickiness, without over-greasiness.

EXAMPLES

The present invention will be described in a more detailed manner by way of examples.

However, these examples should not be construed as limiting the scope of the present invention.

Example 1 and Comparative Examples 1 to 6

[Preparation]

Each of the compositions for hair according to Example 1 (Ex. 1) and Comparative Examples 1 to 6 (Comp. Ex. 1 to Comp. Ex. 6) was prepared by mixing the ingredients shown in Table 1. The numerical values for the amounts of the ingredients are all based on "% by weight" as active raw materials.

TABLE 1

|  | Ex. 1 | Comp. Ex. 1 | Comp. Ex. 2 | Comp. Ex. 3 | Comp. Ex. 4 | Comp. Ex. 5 | Comp. Ex. 6 |
| --- | --- | --- | --- | --- | --- | --- | --- |
| Cyclohexasiloxane (XIAMETER PMX-0246 CYCLOHEXASILOXANE by Dow Corning) | 28 | 28 | 14 | — | 28 | 28 | 70.655 |
| Bis-Cetearylamodimethicone (SILSOFT AX by MOMENTIVE PERFORMANCE MATERIALS) | 1 | 1 | 0.5 | — | 1 | 1 | 1 |
| Dimethicone (XIAMETER PMX-200 SILICONE FLUID 60000CS by Dow Corning) | 1 | 1 | 0.5 | — | 1 | 1 | 1 |
| PEG-12 Dimethicone (XIAMETER OFX-0193 FLUID by Dow Corning) | 2 | 2 | 1 | — | 2 | 2 | 2 |
| Cetrimonium Chloride | 8 | — | 8 | 8 | 8 | 8 | 8 |
| Water | 21.475 | — | 28.275 | 35.075 | 57.975 | 47.975 | 6.47 |
| Hydroxypropylmethyl cellulose | 0.1 | 0.1 | 0.1 | 0.1 | 0.1 | 0.1 | 0.1 |
| PEG-90M | 0.05 | 0.05 | 0.05 | 0.05 | 0.05 | 0.05 | 0.05 |

TABLE 1-continued

|  |  | Ex. 1 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Polyquaternium-47 |  | 1.25 | 1.25 | 1.25 | 1.25 | 1.25 | 1.25 | 125 |
| Polyquaternium-22 |  | 0.625 | 0.625 | 0.625 | 0.625 | 0.625 | 0.625 | 0.625 |
| Propyleneglycol |  | 36.5 | 65.975 | 45.7 | 54.9 | — | 10 | 8.85 |
|  | Presence of water | Yes | No | Yes | Yes | Yes | Yes | Yes |
|  | >20% Silicone oil | Yes | Yes | No | No | Yes | Yes | Yes |
|  | >10% Polyol | Yes | Yes | Yes | Yes | No | Yes | No |
|  | Water/Polyol ≤3 | Yes | Yes | Yes | Yes | No | No | Yes |
| Appearance | Appearance at room temperature | Good | Very Poor | Poor | Good | Very Poor | Very Poor | Very Poor |
| Stability | Stability after 24 hours at room temperature | Good | Good | Poor | Good | Poor | Poor | Poor |
| Wet Combing | Force of wet combing | Good | Poor | Poor | Poor | Good | Poor | Good |
| Volume | $T_0$ Volume/cm width | Good | Poor | Poor | Poor | Poor | Poor | Poor |
| Change | $T_{24}$ Volume/cm width | Good | Poor | Poor | Poor | Poor | Poor | Poor |
| Sensory | Finger through hair when wet | Good | Good | Poor | Poor | Poor | Poor | Poor |
| Evaluation | Smoothness of hair when dry | Good | Good | Poor | Poor | Good | Good | Good |
|  | Moist feeling of hair when dry | Good | Good | Poor | Poor | Good | Good | Good |
|  | Stickiness of hair when dry | Good | Poor | Poor | Poor | Poor | Poor | Poor |

[Evaluations]

(Appearance)

Just after the preparation of the compositions according to Example 1 and Comparative Examples 1 to 6, the appearance of each composition was visually observed at room temperature and categorized in accordance with the following criteria. The results are shown in the line of "Appearance at room temperature" in Table 1.

Good: Transparent
Poor: Translucent
Very Poor: Opaque (Stability)

24 hours after the preparation of the compositions according to Example 1 and Comparative Examples 1 to 6, the appearance of each composition was visually observed at room temperature and categorized in accordance with the following criteria. The results are shown in the line of "Stability after 24 hours at room temperature" in Table 1.

Good: Stable (no separation)
Poor: Unstable (separated)

(Wet Combing)

A wet hair swatch (1 g, 27 cm) to which the same amount of each of the composition according to Example 1 and Comparative Examples 1 to 6 had been applied was placed on a combing machine (Diastron MTT 175 by Dia-Stron Limited UK) and put a comb with a sensor into the hair fibers. Combing was performed by scanning the hair swatch from root to tip, and measured friction force. The measurements were performed 3 times per one wet hair swatch. The same operation was repeated for other two wet hair swatches. In total, the measurements were performed for three hair swatches. The maximum force was selected from the measured data of each hair swatch. The average value of the three maximum forces was calculated and categorized in accordance with the following criteria. The results are shown in the line of "Force of wet combing" in Table 1.

Good: ≤0.12
Poor: >0.12

§ Protocol of Application

The hair swatch was shampooed before application. The hair swatch was placed on a hot plate (30° C.), and then the composition was applied onto the hair swatch and rinsed off under running water.

(Volume Change)

A hair swatch (1 g, 27 cm) to which the same amount of each of the composition according to Example 1 and Comparative Examples 1 to 6 had been applied was dried, and the width of the hair swatch at the middle of the length of the hair swatch was measured just after the drying.

The measured value was categorized in accordance with the following criteria. The results are shown in the line of "To Volume/cm width" in Table 1. Then, the hair swatch was left for 24 hours at 30° C. under 80% humidity. The width of the hair swatch at the middle of the length of the hair swatch was measured again. The measured value was categorized in accordance with the following criteria. The results are shown in the line of "$T_{24}$ Volume/cm width" in Table 1.

Good: <4.5
Poor: ≥4.5

§ Protocol of Application

The hair swatch was shampooed before application. The hair swatch was placed on a hot plate (30° C.), and then the composition was applied onto the hair swatch and rinsed off under running water.

(Sensory Assessments)

Using Japanese slightly bleached hair swatch, the items of finger through hair when wet, smoothness of hair when dry, moist feeling of hair when dry, and stickiness of hair when dry, after the application of each of the composition according to Example 1 and Comparative Examples 1 to 6, were evaluated by 4 panelists in accordance with the following criteria.

5: significantly more
4: more
3: benchmark
2: less
1: significantly less

The average of the scores by the panelists for each sensory assessment was categorized in accordance with the following criteria. The results are shown in the lines of "finger of hair when wet", "smoothness of hair when dry", "moist feeling of hair when dry", and "stickiness of hair when dry" in Table 1.

Good: ≥4
Poor: <4

§ Protocol of Application

The hair swatch was shampooed before application. The hair swatch was placed on a hot plate (30° C.), and then the composition was applied onto the hair swatch and rinsed off under running water. With regard to the evaluation of "smoothness of hair when dry", "moist feeling of hair when dry", and "stickiness of hair when dry", the hair swatch was dried at ambient temperature.

Table 1 shows that the composition according to Example 1 was transparent and stable for a long period of time. The composition according to Example 1 can also provide low wet combing force which results in smooth combing. Table 1 also shows that the composition according to Example 1 can provide excellent volume control effects just after application and 24 hours after the application even under high temperature and humid conditions. Table 1 also shows that the composition according to Example 1 can provide better cosmetic effects to hair under both wet and dry conditions.

The composition according to Comparative Example 1 included no water, and was opaque. The composition according to Comparative Example 1 provided high wet combing force which results in less smooth combing. The composition according to Comparative Example 1 provided poor volume control effects just after application and 24 hours after the application under high temperature and humid conditions. The composition according to Comparative Example 1 provided very sticky feeling to touch when dry conditions.

The composition according to Comparative Example 2 included silicone oils in an amount of less than 20% by weight relative to the total weight of the composition, and was translucent and unstable. The composition according to Comparative Example 2 provided high wet combing force which results in less smooth combing. The composition according to Comparative Example 2 provided poor volume control effects just after application and 24 hours after the application under high temperature and humid conditions. The composition according to Comparative Example 2 provided poor cosmetic effects to hair under both wet and dry conditions.

The composition according to Comparative Example 3 included no silicones, and was transparent and stable. However, the composition according to Comparative Example 3 provided high wet combing force which results in less smooth combing. The composition according to Comparative Example 3 provided poor volume control effects just after application and 24 hours after the application under high temperature and humid conditions. The composition according to Comparative Example 3 provided poor cosmetic effects on hair under both wet and dry conditions.

The composition according to Comparative Example 4 included no polyol, and was opaque and unstable. The composition according to Comparative Example 4 provided low wet combing force which results in smooth combing. However, the composition according to Comparative Example 4 provided poor volume control effects just after application and 24 hours after the application under high temperature and humid conditions. The composition according to Comparative Example 4 provided poor cosmetic effects in terms of finger through hair when wet and stickiness of hair when dry.

The composition according to Comparative Example 5 included polyol but the weight ratio of water/polyol was more than 3, and was opaque and unstable. The composition according to Comparative Example 5 provided high wet combing force which results in less smooth combing. The composition according to Comparative Example 5 provided poor volume control effects just after application and 24 hours after the application under high temperature and humid conditions. The composition according to Comparative Example 5 provided poor cosmetic effects in terms of finger through when wet and stickiness of hair when dry.

The composition according to Comparative Example 6 included polyol but the amount of polyol was less than 10% by weight relative to the total weight of the composition, and was opaque and unstable. The composition according to Comparative Example 6 provided low wet combing force which results in smooth combing. However, the composition according to Comparative Example 6 provided poor volume control effects just after application and 24 hours after the application under high temperature and humid conditions. The composition according to Comparative Example 6 provided poor cosmetic effects in terms of finger through hair when wet and stickiness of hair when dry.

The invention claimed is:

1. A composition for treating keratin fibers, wherein the composition comprises:
   (a) a silicone oil component in an amount of at least 25% by weight, relative to the total weight of the composition;
   (b) water in an amount ranging from 10% to 30% by weight, relative to the total weight of the composition; and
   (c) a polyol selected from glycerin, ethyleneglycol, polyethyleneglycol, propyleneglycol, dipropyleneglycol, butyleneglycol, pentyleneglycol, or hexyleneglycol, wherein:
     the (a) silicone oil component comprises at least one volatile silicone oil and at least one non-volatile silicone oil,
     the total amount of the non-volatile silicone oil(s) in the composition ranges from 1% to 5% by weight, relative to the total weight of the composition,
     the total amount of polyol in the composition ranges from 30% to 40% by weight, relative to the total weight of the composition, and
     the weight ratio of the amount of the (b) water to the amount of the (c) polyol ranges from 0.1 to 3.

2. The composition according to claim 1, wherein the amount of the (a) silicone oil component in the composition is less than or equal to 50% by weight, relative to the total weight of the composition.

3. The composition according to claim 1, wherein the amount of the (a) silicone oil component in the composition is less than or equal to 35% by weight, relative to the total weight of the composition.

4. The composition according to claim 1, wherein the at least one volatile silicone oil is selected from cyclic silicones.

5. The composition according to claim 1, wherein the at least one non-volatile silicone oil is selected from polydimethylsiloxanes, organo-modified polydimethylsiloxanes, or a combination thereof.

6. The composition according to claim 5, wherein the organo-modified polydimethylsiloxane is selected from amodimethicones.

7. The composition according to claim 1, wherein the weight ratio of the amount of the (b) water to the amount of the (c) polyol ranges from 0.3 to 1.

8. The composition according to claim 1, further comprising (d) at least one cationic polymer.

9. The composition according to claim 1, further comprising (e) at least one cationic surfactant.

10. The composition according to claim 1, wherein the at least one volatile silicone oil comprises dodecamethylcyclohexasiloxane.

11. The composition according to claim 5, wherein the organo-modified polydimethylsiloxane is selected from bis-cetearylamodimethicone, dimethicone, PEG-12 dimethicone, or combinations thereof.

12. The composition according to claim 8, wherein the at least one cationic polymer is selected from cationic cellulose derivatives.

13. The composition according to claim 8, wherein the at least one cationic polymer is selected from hydroxyalkylcelluloses.

14. The composition according to claim 8, wherein the at least one cationic polymer is selected from Polyquaternium-5, Polyquaternium-6, Polyquaternium-7, Polyquaternium-10, Polyquaternium-11, Polyquaternium-15, Polyquaternium-16, Polyquaternium-22, Polyquaternium-28, Polyquaternium-44, Polyquaternium-46, Polyquaternium-47, or combinations thereof.

15. The composition according to claim 9, wherein the at least one cationic surfactant is selected from quaternary ammonium salts.

16. The composition according to claim 15, wherein the quaternary ammonium salts are selected from behenyltrimethylammonium chloride, cetrimonium chloride, quaternium-83, quaternium-87, quaternium-22, behenylamidopropyl-2,3-dihydroxypropyldimethylammonium chloride, palmitylamidopropyltrimethylammonium chloride, stearamidopropyldimethylamine, or combinations thereof.

17. A composition for treating keratin fibers, wherein the composition comprises:
    (a) a silicone oil component comprising:
        volatile silicone oil(s) comprising at least one cyclic silicone, and
        non-volatile silicone oil(s) comprising at least one amodimethicone;
    (b) water in an amount ranging from 10% to 30% by weight, relative to the total weight of the composition;
    (c) a polyol selected from glycerin, ethyleneglycol, polyethyleneglycol, propyleneglycol, dipropyleneglycol, butyleneglycol, pentyleneglycol, or hexyleneglycol;
    (d) at least one cationic polymer;
    (e) at least one cationic surfactant; and
    (f) optionally, additional non-volatile silicone oil(s) other than amodimethicones and/or additional volatile silicone oil(s) other than cyclic silicones;
    wherein:
        the silicone oil component is present in the composition in an amount of at least 25% by weight, relative to the total weight of the composition,
        the total amount of non-volatile silicone oil(s) in the composition ranges from 1% to 5% by weight, relative to the total weight of the composition,
        the total amount of polyols in the composition ranges from 30% to 40% by weight, relative to the total weight of the composition, and
        the weight ratio of the amount of water to the total amount of polyol in the composition ranges from 0.1 to 3.

18. The composition according to claim 17, comprising:
    (a) a silicone oil component comprising dodecamethylcyclohexasiloxane and at least one amodimethicone having at least one $C_{12}$-$C_{20}$ alkyl group;
    (b) water;
    (c) propyleneglycol;
    (d) at least one cationic polymer;
    (e) at least one cationic surfactant; and
    (f) optionally, additional non-volatile silicone oil(s) and/or additional volatile silicone oil(s);
    wherein the weight ratio of the amount of water to the total amount of polyol in the composition ranges from 0.2 to 2.

19. A composition for treating keratin fibers, wherein the composition comprises:
    (a) a silicone oil component comprising:
        volatile silicone oil(s) comprising at least one cyclic silicone, and
        non-volatile silicone oil(s) comprising at least one amodimethicone;
    (b) water in an amount ranging from 10% to 30% by weight, relative to the total weight of the composition;
    (c) propyleneglycol in an amount ranging from 30% to 40% by weight, relative to the total weight of the composition;
    (d) at least one cationic polymer; and
    (e) at least one cationic surfactant;
    wherein:
        the silicone oil component is present in the composition in an amount of at least 25% by weight, relative to the total weight of the composition,
        the total amount of non-volatile silicone oil(s) in the composition ranges from 1% to 5% by weight, relative to the total weight of the composition, and
        the weight ratio of the amount of water to the amount of propyleneglycol ranges from 0.1 to 3.

20. The composition according to claim 19, wherein:
    the silicone oil component comprises dodecamethylcyclohexasiloxane and/or at least one amodimethicone having at least one $C_{12}$-$C_{20}$ alkyl group; and
    the weight ratio of the amount of water to the amount of propyleneglycol ranges from 0.2 to 2.

* * * * *